US00PP11509P

United States Patent [19]

Olesen et al.

[11] Patent Number: Plant 11,509

[45] Date of Patent: Sep. 12, 2000

[54] MINIATURE ROSE PLANT NAMED 'POULESTA'

[75] Inventors: L. Pernille Olesen; Mogens N. Olesen, both of Fredensborg, Denmark

[73] Assignee: Poulsen Roser ApS, Fredensborg, Denmark

[21] Appl. No.: 09/122,189

[22] Filed: Jul. 23, 1998

[51] Int. Cl.[7] ..... A01H 5/00

[52] U.S. Cl. ..... Plt./116

[58] Field of Search ..... Plt./116, 121, 122

*Primary Examiner*—Howard J. Locker

[57] ABSTRACT

A new miniature pot rose plant which has abundant, non-fading, lavender-pink flowers. The variety successfully propagates from softwood cuttings and is suitable for year round production in commercial glasshouses. This new and distinct variety has shown to be uniform and stable in the resulting generations from asexual propagation.

1 Drawing Sheet

SUMMARY OF THE DISCOVERY

The present discovery constitutes a new and distinct variety of a miniature pot rose plant which was discovered in a cultivated area. The mutation resulted from 'POULprima', a miniature pot rose hybridized by the same inventors. 'POULprima' is described and illustrated in U.S. Plant Pat. No. 9,482, and issued on Mar. 26, 1996. The new rose variety resulted from a naturally occurring mutation of unknown causation on a branch of 'POULprima'.

The rose plant of the present discovery has a unique combination of characteristics which are outstanding in the new variety and which distinguish it from the original rose 'POULprima' as well as all other varieties which we are aware of. For example, the new variety has:

1. Abundant, lavender-pink, very double flowers;
2. Vigorous and compact growth,
3. Year-round flowering under glasshouse conditions;
4. Suitability for production from softwood cuttings in pots;
5. Durable flowers and foliage which make the variety suitable for distribution in the floral industry.

This combination of qualities is not present in previously available commercial cultivars of this type and distinguish 'POULesta' from all other varieties of which we are aware.

The resulting mutation was selected and evaluations were conducted on the resulting rose plants in a controlled environment.

Asexual reproduction of 'POULesta' by cuttings was first done by L. Pernille and Mogens N. Olesen in their nursery in Fredensborg, Denmark in March, 1996. This initial and other subsequent propagations have demonstrated that the characteristics of 'POULesta' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, stems, and a plant of 'POULesta'. Specifically illustrated in SHEET 1:

1. Stem or entire plant showing branching and the attachment of leaves, buds, and peduncles;
2. Flower bud, partially opened bud, and open bloom;
3. Flower petals, detached;

4. Sepals, receptacle, and pedicel;
5. Flowering stem as well as a bare stem exhibiting thorns;
6. Leaves.

DETAILED DESCRIPTION OF THE VARIETY

The following is a detailed description of 'POULesta', as observed in its growth in glasshouses in Fredensborg, Denmark and Half Moon Bay, Calif., and in field nursery in Jackson County, Oreg. Color references are made using The Royal Horticultural Society (London, England) Colour Chart, 1995, except where common terms of color are used.

For a comparison, the nearest existing rose variety is 'POULprima', a miniature rose variety from the same inventors described and illustrated in U.S. Plant Pat. No. 9,482 and issued on Mar. 26, 1996. Chart 1 details several physical characteristics of POULesta and POULprima.

CHART 1

| | 'POULesta' | 'POULprima' |
|---|---|---|
| Petal count | 55–65 petals | 30–35 petals |
| Bud color at ¼ open | Red-Purple Group 64B | Red-Purple Group 61C |
| Color of upper surface of flower petal on an open flower | Red-Purple Group 67C | Red-Purple Group 61C |
| Basal petal spot | Outer petals: Green-Yellow Group 1B<br>Inner petals: Yellow-Orange Group 14B | Outer petals: Yellow Group 4C<br>Inner petals: Yellow Group 4A |

Parentage: Mutation of 'POULprima'.

Classification:

*Botanical.*—Rosa hybrida.

*Commercial.*—Miniature.

FLOWER AND FLOWER BUD

Blooming cycle: Continuous.

Flower bud:

*Size.*—14–16 mm in length when petals are just beginning to crack open.

*Bud form.*—Pointed ovoid.

*Bud colors.*—As sepals unfold, Red-Purple Group 63A. Red-Purple Group 64B at ¼ opening.

*Sepals.*—Between 139B and 139C of Green Group. Weak foliaceous appendages on three of the five sepals. All five sepals with stipitate glands present on margins and exterior surfaces. Very limited number of short fine hairs present.

*Peduncle.*—Surface Moderate number of stipitate glands. Length: Short, 15 mm–25 mm. Color: Green Group 143C to Yellow-Green Group 144B. Strength: Upright.

*Receptacle.*—Surface: Smooth. Shape: Broadly urn-shaped. Size: Medium. 5 mm×6 mm. Color: Green Group 143B.

*Borne.*—Generally 2–5 buds per flowering stem.

Flower bloom:

*Size.*—Medium for a 10 cm pot rose. Average diameter is 40 mm when open.

*Form.*—Upon opening: form of upper part of flower is high centered. Completely open, form of upper part of flower is flat with outermost petals reflexing backwards.

*Petalage.*—Double. Average range: 55–65 under normal conditions.

*Color.*—Upon opening, the upper surface of the petals is Red Purple Group 67B. Upon opening, the reverse petal surface is Red-Purple Group 67C. After opening, the upper petal surface is Red-Purple Group 67C. After opening, the reverse petal surface is Red-Purple Group 57C. Upon opening, a petal spot Greens- Yellow Group 1B exists on the inner and outer bases of the outermost petals. Upon opening, a petal spot Yellow-Orange Group 14B exists on the inner and outer bases of the innermost petals. After opening, the petal spot is Green-Yellow Group 1C on the bases of the outermost petals. After opening, the petal spot is Yellow Group 12B on the bases of the innermost petals.

*General tonality.*—No change in the general tonality at the end of the first day. At the end of 8–10 days, there is a slight change to Red-Purple Group 57C.

*Petal reflex.*—Innermost petals reflexed slightly. Outermost petals reflex to form a double point.

*Petal edge.*—Pointed at center.

*Petaloids.*—Present. Quantity: 10–15.

*Fragrance.*—Light.

*Duration.*—As a pot plant, flowers last from 15 to 18 days. As a cut flower 8 to 12 days.

Petals:

*Texture.*—Thick.

*Shape.*—Rounded to deltoid.

*Form.*—Reflexed slightly.

*Arrangement.*—Imbricated.

Reproductive Organs:

*Pollen.*—Color: Yellow Group 11A. Abundance: Average.

*Anthers.*—Size: Medium. Color: Yellow Group 11A. Abundance: Limited to abundant. Variable.

*Filaments.*—Color: Green-Yellow Group 1B.

*Stigmas.*—Positioned only slightly superior to anthers. Some flowers lacking complete pistils. Color: Green-White Group 157A.

*Styles.*—Color: Green-White Group 157A.

PLANT

Plant growth: Vigorous, compact, upright to bushy. When grown as a 10 cm pot plant, the average height of the plant itself is 18 cm and the average width is 18–20 cm. When grown as a nursery plant on its own roots the average plant height is 25–35 cm and the average plant width is 20–25 cm.

Stems:

*Color.*—Young wood: Yellow-Green Group 144B. Older wood: Green Group 143C.

*Prickles.*—Incidence: Average number of thorns. Some stems with stiff hairs. Size: Average length: 3 mm–4 mm. Color: Greyed-Green Group 193A. Shape: Linear to slightly curved.

*Bark.*—Young wood: Smooth. Older wood: Smooth.

Plant foliage: Normal number of leaflets on normal leaves in middle of stem: 5 leaflets.

*Leaf size.*—Medium. 70 mm×50 mm.

*Abundance.*—Abundant.

*Color.*—Upper Leaf Surface: Green Group 137A to Yellow-Green Group 147A. Lower Leaf Surface: Green Group 138B. Juvenile foliage: Green Group 143A to 143B. No anthocyanin coloration observed.

Plant leaves and leaflets:

*Stipules.*—Present. Size: 8 mm–10 mm. Color: Green Group 143A.

*Petiole.*—Length: 16 mm to 18 mm. Underneath: Without prickles. Color: Green Group 137A. Edges: With stipitate glands.

*Rachis.*—With small prickles underneath. Color: Green Group 137A.

*Leaflet edge.*—Finely serrated.

*Shape.*—Leaflets are pointed ovate.

*Leaflets.*—Number: 5.

*Other.*—Moderately glossy.

Disease resistance: Above average resistance to mildew and Botrytis under normal growing conditions in Half Moon Bay, Calif. and Fredensborg, Denmark.

We claim:

1. A new and distinct variety of rose plant of the miniature class, substantially as herein illustrated and described as a distinct and novel rose variety due to its abundant flowers, vigorous and compact growth, year round flowering under glasshouse conditions, suitability for production from softwood cuttings in pots, and durable flowers and foliage which make the variety suitable for distribution in the floral industry.

* * * * *

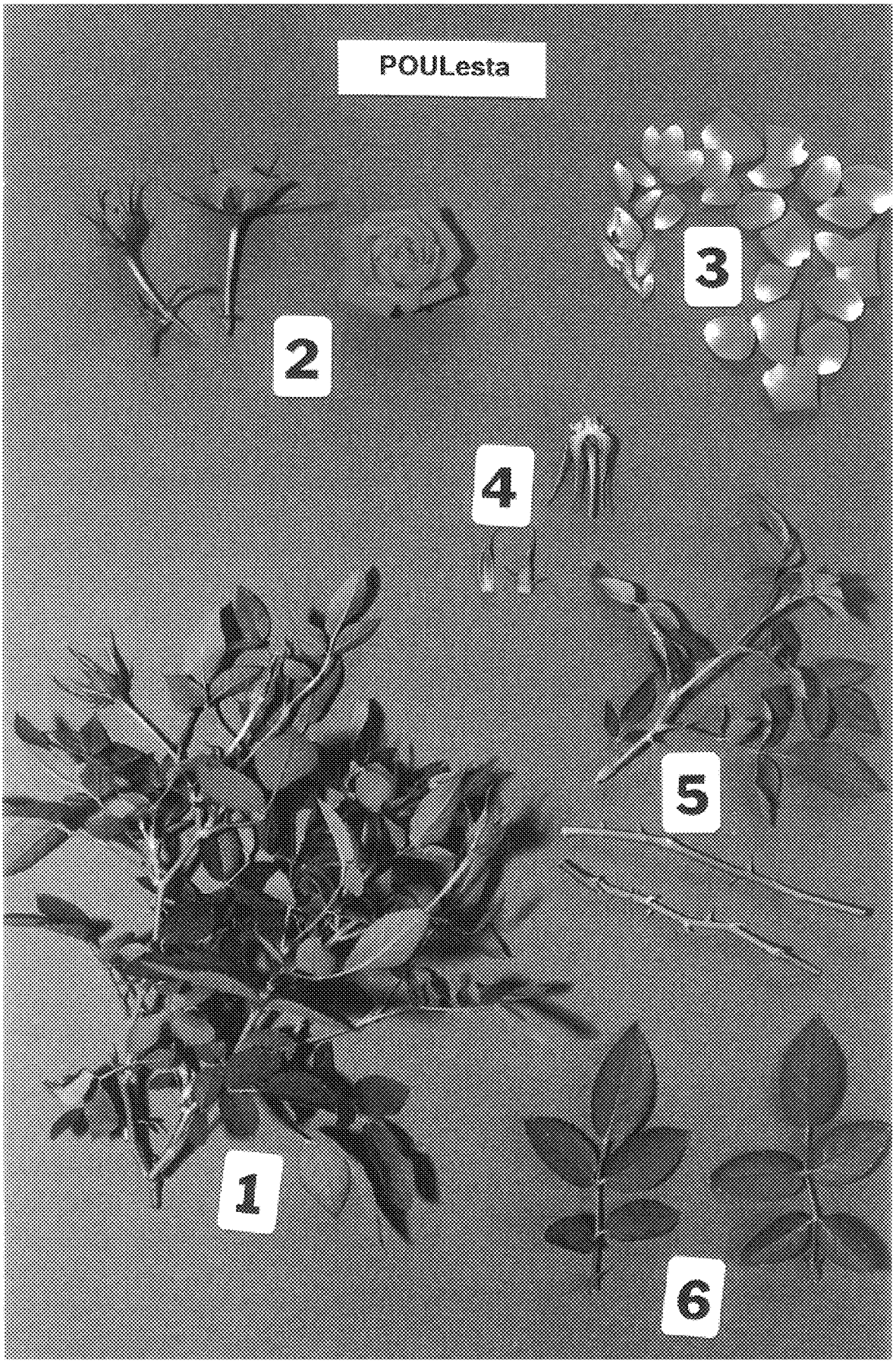
POULesta
1
2
3
4
5
6